(12) United States Patent
Enomoto et al.

(10) Patent No.: US 9,795,896 B2
(45) Date of Patent: *Oct. 24, 2017

(54) ADSORPTION METHOD, ADSORPTION SEPARATION METHOD, AND DRUG DELIVERY CARRIER

(71) Applicant: Koito Manufacturing Co., Ltd., Minato-ku, Tokyo (JP)

(72) Inventors: Kiminori Enomoto, Shizuoka (JP); Hisayoshi Daicho, Shizuoka (JP); Yu Shinomiya, Shizuoka (JP)

(73) Assignee: KOITO MANUFACTURING CO., LTD., Minato-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/658,352

(22) Filed: Mar. 16, 2015

(65) Prior Publication Data

US 2015/0182876 A1 Jul. 2, 2015

Related U.S. Application Data

(63) Continuation of application No. PCT/JP2013/005243, filed on Sep. 4, 2013.

(30) Foreign Application Priority Data

Sep. 18, 2012 (JP) .................................. 2012-203966

(51) Int. Cl.

| A61K 6/033 | (2006.01) |
|---|---|
| B01D 15/36 | (2006.01) |
| C01B 25/32 | (2006.01) |
| A61K 47/02 | (2006.01) |
| A61K 9/00 | (2006.01) |
| B01J 20/04 | (2006.01) |
| B01J 20/30 | (2006.01) |
| B01J 20/28 | (2006.01) |
| B01J 20/02 | (2006.01) |
| A61K 9/70 | (2006.01) |

(52) U.S. Cl.
CPC .......... *B01D 15/362* (2013.01); *A61K 9/0092* (2013.01); *A61K 9/70* (2013.01); *A61K 47/02* (2013.01); *B01D 15/36* (2013.01); *B01J 20/0207* (2013.01); *B01J 20/0292* (2013.01); *B01J 20/048* (2013.01); *B01J 20/28004* (2013.01); *B01J 20/28042* (2013.01); *B01J 20/3071* (2013.01); *B01J 20/3078* (2013.01); *C01B 25/32* (2013.01)

(58) Field of Classification Search
CPC ...... A61K 6/0085; A61K 47/42; A61K 6/033; A61K 2800/56; A61K 33/42
See application file for complete search history.

(56) References Cited

U.S. PATENT DOCUMENTS

| 6,344,209 B1 * | 2/2002 | Saito ..................... A61K 47/26 424/426 |
|---|---|---|
| 7,837,872 B2 | 11/2010 | Kobayashi et al. |
| 8,470,724 B2 * | 6/2013 | Taira ........................ B28B 1/00 252/584 |
| 2005/0175788 A1 * | 8/2005 | Nonami ................. B01J 21/063 427/430.1 |
| 2006/0207940 A1 | 9/2006 | Kobayashi et al. |
| 2010/0055019 A1 * | 3/2010 | Day ......................... A61K 33/42 423/309 |
| 2010/0234577 A1 | 9/2010 | Mazzola et al. |
| 2011/0178276 A1 * | 7/2011 | Cummings ........ B01D 15/3847 530/387.1 |

FOREIGN PATENT DOCUMENTS

| CN | 1961973 A | 5/2007 | |
|---|---|---|---|
| CN | 102491300 A | 6/2012 | |
| EP | 2837715 A1 | 2/2015 | |
| JP | EP 0722772 A1 * | 7/1996 | ........... G01N 30/482 |
| JP | 09-169794 A | 6/1997 | |
| JP | 2005-313150 A | 11/2005 | |
| JP | 2006-239660 A | 9/2006 | |
| JP | 2008-056513 A | 3/2008 | |
| JP | 2010-510963 A | 4/2010 | |
| JP | WO 2010140634 A1 * | 12/2010 | ............. C01B 25/32 |
| JP | 2011-011971 A | 1/2011 | |
| WO | 2009/017491 A1 | 2/2009 | |
| WO | 2010/140634 A1 | 12/2010 | |

OTHER PUBLICATIONS

SRM University. PH 0101 Unit 4 Lecture 1. Date retrieved: Sep. 13, 2016. Slide 6.*
University of Virginia. Chapter 3: Structure of Crystals. Date retrieved: Sep. 13, 2016. <http://www.virginia.edu/bohr/mse209/chapter3.htm>.*
International Search Report (Form PCT/ISA/210) issued on Dec. 10, 2013, in corresponding International Application No. PCT/JP2013/005243, and an English Language translation. (7 pages).
International Preliminary Report on Patentability (Form PCT/IB/373) issued on Mar. 24, 2015 and the Written Opinion of the International Searching Authority (Form PCT/ISA237) issued on Dec. 12, 2013, in corresponding International Application No. PCT/JP2013/005243 (12 pages).
Hui et al., "Monodisperse F-Substituted Hydroxyapatite Single-Crystal Nanotubes with Amphiphilic Surface Properties," Inorganic Chemistry, (2009), vol. 48, No. 13, p. 5614-5616.

(Continued)

*Primary Examiner* — Tracy Lu
(74) *Attorney, Agent, or Firm* — Buchanan Ingersoll & Rooney PC

(57) ABSTRACT

An adsorption method adsorbs a substance by using a tube-shaped apatite crystal. The apatite crystal may be a monocrystal given by a general formula $M^2_5(PO_4)_3X$ ($M^2$ denotes at least one element selected from the group consisting of divalent alkali earth metal and Eu, and X denotes at least one element or molecule selected from the group consisting of halogen element and OH). The outer form of the apatite crystal may be a hexagonal prism in which the aperture of a hole formed on a top surface or bottom surface of the hexagonal prism may be hexagonal.

7 Claims, 1 Drawing Sheet

(56) References Cited

OTHER PUBLICATIONS

Ma et al., "Solvothermal Preparation of Hydroxyapatite Microtubes in water/N,N-dimethylformamide Mixed Solvents," Materials Letters, (2008), vol. 62, No. 10-11, pp. 1642-1645.
Office Action issued on Jan. 5, 2016, by the Chinese Patent Office in corresponding Chinese Patent Application No. 201380048258.2, and an English Translation of the Office Action. (17 pages).
Extended Search Report issued by the European Patent Office in corresponding European Patent Application No. 13838444.1 on Apr. 13, 2016 (9 pages).
Office Action issued by the European Patent Office on Jan. 18, 2017, in corresponding European Patent Application No. 13838444.1 (5 pages).
Decision of Refusal issued by the Korean Intellectual Property Office on Dec. 29, 2016, in corresponding Korean Patent Application No. 10-2015-7009825 and an English translation of the Decision (12 pages).
Yuyongxian, "Synthesis and Properties of Eu5(PO4)3OH", Journal of Baotou University of Iron and Steel Technology, Mar. 1995, pp. 15-18, vol. 14, No. 1.
Office Action (Second Office Action) issued on Aug. 29, 2016, by the Chinese Patent Office in corresponding Chinese Patent Application No. 2013800482582, and an English Translation of the Office Action. (18 pages).
Office Action (Notification of Reason(s) for Refusal) issued on Jun. 16, 2016, by the Korean Patent Office in corresponding Korean Patent Application No. 10-2015-7009825, and an English Translation of the Office Action. (13 pages).
Office Action (Notification of Reason(s) for Refusal) issued on Jun. 6, 2017, by the Japanese Patent Office in corresponding Japanese Patent Application No. 2014-536577 and an English Translation of the Office Action. (6 pages).
Decision of Refusal issued Feb. 14, 2017, by the Korean Patent Office in corresponding Korean Patent Application No. 10-2015-7009825 and an English translation of the Office Action (11 pages).
Office Action (The Fourth Office Action) issued on Aug. 8, 2017 by the State Intellectual Property Office of People's Republic of China in corresponding Chinese Patent Application No. 201380048258.2 and an English Translation of the Office Action. (19 pages).
Rendón-Angeles et al., "Topotaxial Conversion of Chlorapatite and Hydroxyapatite to Fluorapatite by Hydrothermal Ion Exchange," Chemistry of Materials, (2000), vol. 2, No. 8, 2143-2150.

\* cited by examiner

ADSORPTION METHOD, ADSORPTION SEPARATION METHOD, AND DRUG DELIVERY CARRIER

CROSS-REFERENCE TO RELATED APPLICATIONS

This application is based upon and claims the benefit of priority from the prior Japanese Patent Application No. 2012-203966, filed on Sep. 18, 2012 and International Patent Application No. PCT/JP2013/005243, filed on Sep. 4, 2013, the entire content of each of which is incorporated herein by reference.

BACKGROUND OF THE INVENTION

1. Field of the Invention

The present invention relates to crystalline apatite applicable in an extensive field as a functional material.

2. Description of the Related Art

Hydroxyapatite is known to have adsorption capacity for protein and amino acid. Technologies exploiting this capacity and utilizing an apatite adsorbent to isolate or purify protein or amino acid have been proposed (see, for example, patent documents 1-3).

[patent document 1] JP9-169794
[patent document 2] JP2005-313150
[patent document 3] JP2006-239660

However, the related-art apatite crystal has a shape of a needle, plate, bar, etc. so that there is room for improvement in terms of adsorption capacity.

SUMMARY OF THE INVENTION

The present invention addresses this requirement and a purpose thereof is to provide a novel adsorption method with improved adsorption capacity.

To address the aforementioned issue, the adsorption method according to an embodiment of the present invention adsorbs a substance by using a tube-shaped apatite crystal.

Optional combinations of the aforementioned constituting elements, and implementations of the invention in the form of methods, apparatuses, and systems may also be practiced as additional modes of the present invention.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION OF THE INVENTION

Figure 1:
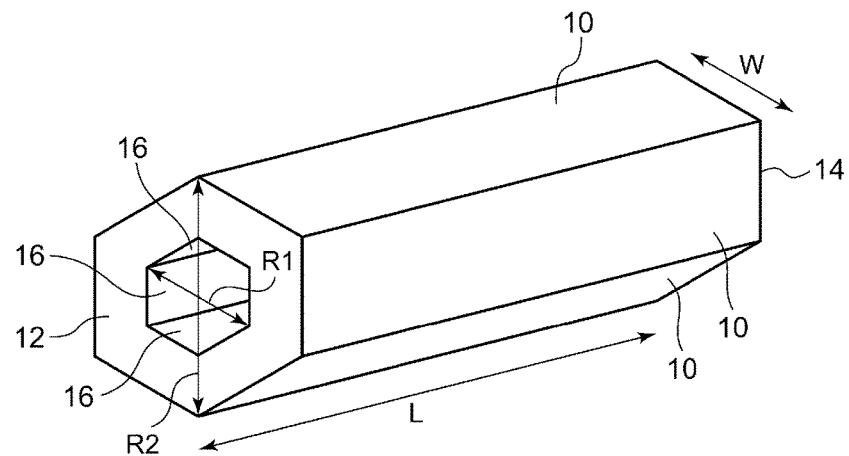
FIG. 1 is a schematic diagram showing the structure of a tube-shaped apatite monocrystal.

An adsorption method according to an embodiment of the present invention adsorbs a substance by using a tube-shaped apatite crystal. The apatite crystal according to this embodiment is tubular so that the specific surface area thereof is larger than that of the related-art needle-shaped or plate-shaped apatite crystals. Therefore, the capacity to adsorb a substance is increased. Consequently, a larger amount of substance can be adsorbed by using the tube-shaped apatite crystal.

The apatite crystal may be a monocrystal given by a general formula $M^2_5(PO_4)_3X$ ($M^2$ denotes at least one element selected from the group consisting of divalent alkali earth metal and Eu, and X denotes at least one element or molecule selected from the group consisting of halogen element and OH).

A monocrystal given by a general formula $M^2_5(PO_4)_3OH$ ($M^2$ denotes at least one element selected from the group consisting of divalent alkali earth metal and Eu) may be used to adsorb protein or amino acid. In this way, biological polymers such as protein and amino acid can be adsorbed efficiently.

The outer form of the apatite crystal may be a hexagonal prism in which the aperture of a hole formed on the top surface or bottom surface of the hexagonal prism is hexagonal. Use of a tube-shaped monocrystal having a shape of hexagonal prism, which is relatively easy to manufacture, provides a large specific surface area.

The inner diameter of the tube-shaped apatite crystal may be 10 nm to 10 μm. This can properly adsorb protein or amino acid in a hole of the apatite crystal.

Another embodiment of the present invention relates to an adsorption separation method. The method comprises adsorbing protein or amino acid by using a tube-shaped apatite crystal, causing the apatite crystal on which the protein or amino acid is adsorbed to contact an aqueous chloride solution, and selectively isolating the adsorbed protein or amino acid.

According to this embodiment, the protein or amino acid can be selectively isolated from a mixture containing the protein or amino acid.

The invention will now be described by reference to the preferred embodiments. This does not intend to limit the scope of the present invention, but to exemplify the invention.

A description will be given of embodiments of the present invention.

[Apatite Crystal]

The apatite crystal suitable for the adsorption method according to the embodiment is a tube-shaped apatite monocrystal. The apatite crystal is given by a general formula $M^2_5(PO_4)_3X$ ($M^2$ denotes at least one element selected from the group consisting of a divalent alkali earth metal and Eu, and X denotes at least one element or molecule selected from the group consisting of a halogen element and OH). For example, the alkali earth metal may be Ca, Sr, Ba, Ra, Mg, or Be. The halogen element may be, for example, F, Cl, Br, or I.

[Method of Manufacturing a Tube-Shaped Apatite Monocrystal]

A description will be given of a method of manufacturing a tube-shaped monocrystal of apatite by way of examples.

Example 1

First, $CaHPO_4$, $CaCO_3$, and $CaCl_2$ are metered and mixed uniformly at a molar ratio of 5:3:1. Thereafter, NaCl is added so that the chlorapatite concentration is 0.15 mol %. The mixture is heated to 800-1100° C. in a platinum crucible at a temperature increase rate 100-500° C./h. Synthesis is allowed to proceed for 48 hours at a synthesis temperature of 800-1100° C. and then the temperature is lowered from 800-1100° C. to 500° C. at a temperature decrease rate 5-300° C./h. Thereafter, the synthesized product is cooled naturally to a normal temperature. After calcination, the product is cleaned carefully using pure hot water (about 80° C.) to extract a chlorapatite monocrystal.

The chlorapatite monocrystal (20 mg) is heated in a kiln to 900-1300° C. Water vapor is introduced in the kiln and induces a reaction over a period of about 2 weeks, thereby converting the chlorapatite monocrystal into a hydroxyapatite monocrystal.

Example 2

The same method as used in Example 1 is used to obtain a chlorapatite monocrystal. Thereafter, the chlorapatite monocrystal (20 mg) is introduced in a platinum capsule (2.6 mmφ, length=3.3 mm) along with a 6.25 (mol/L) aqueous solution (40 µl) of potassium hydroxide (KOH), and the capsule is sealed. The hydrothermal process is performed in an autoclave of test tube type by using water as a pressure medium under the condition of 100 MPa. The temperature increase rate is 20° C. per minute. The processing temperature is constantly 400° C. and the processing time is 48 hours. This obtains a hydroxyapatite monocrystal.

[Crystal Structure of Apatite]

Apatite is an ion crystal that belongs to the hexagonal system. An apatite monocrystal usually has a hexagonal prism shape. FIG. 1 is a schematic diagram showing the structure of a tube-shaped apatite monocrystal according to the embodiment. As shown in FIG. 1, the apatite monocrystal according to the embodiment is tubular and the outer form of the crystal is a hexagonal prism. The aperture of a hole formed on the top surface or bottom surface of the hexagonal prism is hexagonal. For this reason, the thickness of the tube outer wall is uniform. Further, the hole formed in the hexagonal prism may be a through hole.

The specific surface area ($cm^2/g$) of the tube-shaped apatite crystal is 1.5-4 times larger than that of the related-art needle-shaped apatite crystal. Thus, a hexagonal tube-shaped monocrystal, which is relatively easy to manufacture, provides a large specific surface area. This allows a fluid that contains a substance adsorbed by the adsorption method described later to contact the crystal surface efficiently.

Tube-shaped monocrystals of different sizes and shapes may be used as an adsorbent, depending on the application. For example, the inner diameter R1 of the opening of the tube-shaped monocrystal may be about 10 nm-60 µm. The diameter (outer diameter R2) of the tube-shaped monocrystal is about 20 nm-100 µm. The length L of the tube-shaped monocrystal in the longitudinal direction is about 50 nm-4 mm.

[Adsorption Method for Substance]

A description will be given of a method of adsorbing a substance using the tube-shaped apatite crystal described above.

According to the adsorption method of the embodiment, a column is filled by the aforementioned tube-shaped apatite monocrystal. A fluid (liquid) that contains a substance subject to adsorption is allowed to pass through the column so that the substance is adsorbed.

Where an adsorbent with a small particle diameter is selected to fill a column in order to increase the specific surface area, clogging is likely to occur and fluid permeability may not be secured. Meanwhile, use of an adsorbent with a large particle diameter to secure fluid permeability results in a smaller specific area and a decrease in the overall adsorption capacity.

By way of contrast, the adsorption method according to the embodiment uses a tube-shaped apatite crystal as an adsorbent. This ensures high permeability by allowing the fluid to pass through the hollow portion (through hole) even if the filling factor of the adsorbent in the column is increased. An added advantage is that, because the apatite crystal is tubular, the specific surface area is larger than that of the related-art needle-shaped or plate-shaped apatite crystals so that the capacity to adsorb a substance is increased. Thus, by using the tube-shaped apatite crystal such as that described above, the specific surface area can be increased and a larger amount of substance can be adsorbed without decreasing the fluid permeability.

[Adsorption Method for Protein, etc.]

A description will be given of a case where protein or amino acid is adsorbed by using hydroxyapatite, which is one type of apatite.

A monocrystal given by a general formula $M^2{}_5(PO_4)_3OH$ ($M^2$ denotes at least one element selected from the group consisting of divalent alkali earth metal and Eu) may be used to adsorb protein or amino acid. The monocrystal can adsorb biological polymers such as protein and amino acid efficiently.

The reason for this will be given below. As described above, hydroxyapatite belongs to the hexagonal system in crystal structure. A monocrystal of hydroxyapatite is of a hexagonal prism shape. As shown in FIG. 1, a monocrystal of a hexagonal prism shape has lateral surfaces 10 which are a-plane surfaces, and an upper surface 12 and a lower surface 14, which are c-plane surfaces. A-planes are richly populated by adsorption sites formed by positively-charged calcium ions, and c-planes are richly populated by adsorption sites formed by negatively-charged phosphoric ions. For this reason, an acidic protein or amino acid, which are rich in carboxyl groups or phosphoric groups, are likely to be adsorbed by the a-planes.

The tube-shaped hydroxyapatite crystal according to the embodiment has 6 interior lateral surfaces 16 that define the interior wall of the through hole, other than the 6 lateral surfaces 10 of the hexagonal prism. The interior lateral surfaces 16 are also a-planes. For this reason, not only the tube-shaped apatite crystal has a larger specific surface area than the related-art needle-shaped or plate-shaped apatite crystal but also the proportion occupied by the a-planes is larger than that of the related-art crystal. Accordingly, the adsorption method according to the embodiment, in which the tube-shaped hydroxyapatite crystal is used, can further improve the adsorption capacity for protein and amino acid.

Ordinary protein (e.g., hemoglobin, which contains 574 amino acids) has a diameter of about 5 nm. Therefore, a tube-shaped hydroxyapatite crystal having an inner diameter of 10 nm-10 µm is preferable as an adsorbent for protein. Because the average diameter of an ordinary amino acid molecule is about 0.5 nm, a tube-shaped hydroxyapatite crystal having an inner diameter of about 10 nm-1 nm, which is smaller than that of adsorbent for protein, is preferable as an adsorbent to adsorb amino acid. In this way, protein or amino acid can be properly adsorbed in the hole of the apatite crystal.

[Adsorption Method for Heavy Metal, etc.]

Hydroxyapatite has the adsorption capacity for heavy metals (lead, cadmium, mercury, etc.), fluorine, and aldehydes. The adsorption capacity for heavy metals derive from the ion exchange capacity of the apatite. The a-planes rich in Ca ions are superior to the other planes. Hydroxyapatite adsorbs heavy metals by replacing heavy metals such as lead and mercury with calcium ions in the structure. For this reason, the tube-shaped hydroxyapatite crystal having Ca ion-rich a-planes on the tube interior wall surface is more advantageous in adsorbing heavy metals than an adsorbent using the related-art needle-shaped apatite crystal. The tube-shaped hydroxyapatite crystal according to the embodiment is thermally stable. Even when aldehydes are adsorbed, the adsorbed component is not detached when heated to 60-80° C.

[Adsorption Method for Lipid, etc.]

Hydroxyapatite has high adsorption capacity for lipid, lipid peroxide, and sugar. Conceivably, this is because lipid and sugar are negatively charged and so are preferentially adsorbed on the positively-charged a-plane. For this reason, the tube-shaped hydroxyapatite crystal having Ca ion-rich a-planes on the tube interior wall surface is more advantageous than an adsorbent using the related-art needle-shaped apatite crystal in adsorbing lipid or sugar.

[Adsorption Separation Method]

A variation of the embodiment relates to an adsorption separation method. The method includes adsorbing protein or amino acid using the aforementioned tube-shaped apatite crystal, causing the apatite crystal on which the protein or amino acid is adsorbed to contact an aqueous chloride (e.g., NaCl) solution, and selectively isolating the adsorbed protein or amino acid. According to this embodiment, the protein or amino acid can be selectively isolated from a mixture containing the protein or amino acid.

[Drug Delivery System]

Another variation of the embodiment relates to a drug carrier that can be used as a drug delivery system. The drug carrier can be implemented by using the adsorbing action of the aforementioned tube-shaped apatite crystal and by causing the apatite crystal to carry a drug. Performance requirements for the drug carrier used in a drug delivery system include (1) capability to carry a large amount of drug and (2) capability for sustained release of the drug.

For example, apatite as a biomaterial is preferred as a carrier used in a drug delivery system for a bone. Known apatites as a biomaterial are spherical or columnar (solid columns) so that there is room for improvement in respect of the amount carried and capability for sustained release. However, the aforementioned tube-shaped apatite we have developed can be more successfully applied to a drug delivery system.

By way of example, the tube-shaped apatite crystal given by a general formula $M^2{}_5(PO_4)_3X$ may be used as a carrier in a drug delivery system. For example, the size of a carrier embodied by a tube-shaped apatite crystal is such that the outer diameter is 20 nm-50 nm, the inner diameter is 10 nm-50 nm, and the length is 50 nm-50 μm. The carrier is transported into the body, maintaining a predetermined component (e.g., active substance) adsorbed (absorbed) and carried by the carrier, and delivers the substance to a desired site before releasing the substance.

The performance of an apatite crystal as a biomaterial to carry or adsorb a drug can be improved by affinity of various substances. For example, an apatite crystal has a capacity to bond with water, charged particles, lipid, protein, nucleic acid, etc. The capacity allows a drug to be carried by the crystal. For the purpose of carrying a large amount of drug, the larger the specific surface area of the carrier, the better.

Tube-shaped apatite crystals are suited to this purpose. Crystals with smaller tube diameter (inner diameter) are more suitable. For the purpose of sustained release, the drug should preferably be carried inside the tube rather than on the surface of a particle. The specific surface area of a tube-shaped crystal is 1.5-4 times that of the related-art solid apatite particle so that the capacity to adsorb a drug is improved 1.5-4 times. Based on the foregoing, it should be appreciated that the use of a tube-shaped apatite crystal as a biomaterial in a drug delivery system is advantageous.

In terms of the dosage form, the apatite crystal for carrying a drug can be effectively used for (a) oral dosage, intravenous injection, hypodermic injection, lung administration, and nasal administration, by adjusting the size of the crystal. Functionally, the crystal can be used to (b) selectively deliver the drug to the liver, lung, inflamed region, etc. and to improve release control of the drug.

A description will now be given of evaluation of the performance of the apatite crystal to carry a drug. In an example described below, the tube-shaped apatite crystal manufactured by the method as described in Example 1 is used as a carrier for drug delivery. In a comparative example, the related-art needle-shaped apatite crystal is used as a drug delivery carrier. The tube-shaped apatite crystal according the example has a length of 200 nm, an outer diameter of 40 nm, and an inner diameter of 20 μm.

The needle-shaped apatite monocrystal according to the comparative example is manufactured by the following method. A 0.5 mol/L aqueous solution of phosphoric acid is dropped in a 0.3 mol/L suspended calcium hydrate liquid. A monocrystal precipitate is obtained by adjusting pH to 5-9 to promote formation of a monocrystal. By allowing the precipitate to grow for 48 hours at 1200° C., a needle-shaped hydroxyapatite monocrystal having a length of 200 μm and an outer diameter of 40 μm was obtained.

Ultrasonic vibration (frequency 28 kHz, output 100 W) was applied for five minutes to a mixture of 10 mg of the tube-shaped apatite crystal of the example and 1 ml of acetonitrile, so as to obtain a suspended liquid. Similarly, ultrasonic vibration (frequency 28 kHz, output 100 W) was applied for five minutes to a mixture of 10 mg of the tube-shaped apatite crystal of the example and 1 ml of acetonitrile, so as to obtain a suspended liquid.

Subsequently, each suspended liquid is subject to centrifugal separation (9000×g, 20° C., 3 minutes). The supernatant was further filtered using a filter of 0.22 μm and the resultant liquid is used as a sample for high-performance liquid chromatography. The high-performance liquid chromatography demonstrated that itraconazole (active pharmaceutical ingredient) is contained in the amount 0.80 mg in 10 mg of the carrier according to the comparative example, and that itraconazole is contained in the amount 1.40 mg in 10 mg of the carrier according to the example. In other words, the adsorption rate of the carrier according to the comparative example is 8.0% and the adsorption rate of the carrier according to the example is 14.0%.

Figure 2:
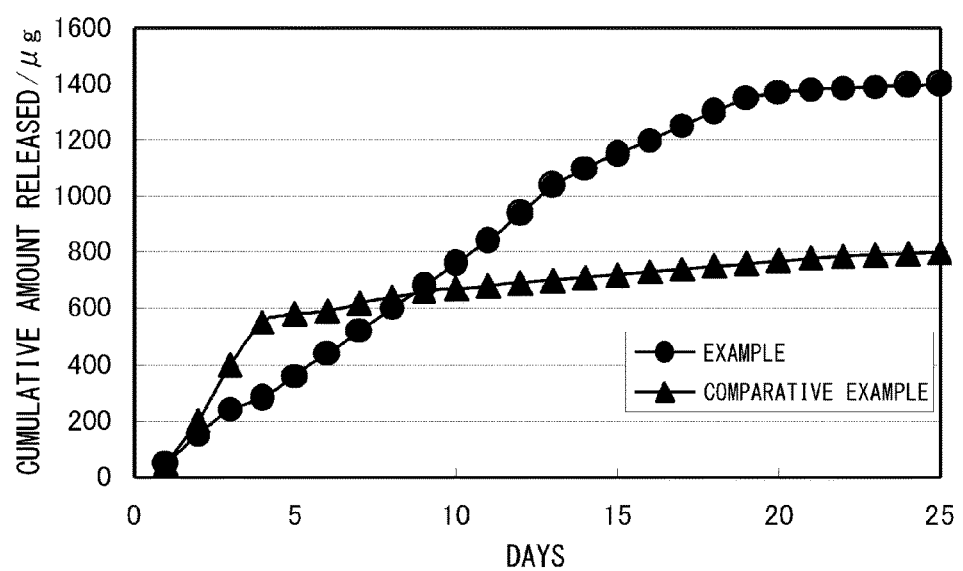
FIG. 2 is a graph showing results of a sustained drug release test using the drug delivery carriers according to the example and the comparative example.

A description will now be given of a sustained drug release test. FIG. 2 is a graph showing results of a sustained drug release test using the drug delivery carriers according to the example and the comparative example. The sustained drug release test is conducted by placing the drug delivery carrier carrying the drug in 0.1 mg of phosphate buffer (pH7.4) at 37° C. and sampling the buffer solution every day. The sampled buffer solution is analyzing using high-performance liquid chromatography and the cumulative amount of itraconazole released from the drug delivery carrier is calculated.

As shown in FIG. 2, the amount of drug release per day from the drug delivery carrier according to the comparative example is larger until about the 4th day but is rapidly decreased thereafter. Meanwhile, in the case of the drug delivery carrier according to the example, the stable sustained release performance is maintained until about the 20th day. Therefore, the drug delivery carrier according to the example is capable of delivering the drug to a desired affected site in a stable manner and over a long period of time.

The embodiments of the present invention are not limited to those described above and appropriate combinations or replacements of the features of the embodiments are also encompassed by the present invention. The embodiments may be modified by way of combinations, rearranging of the processing sequence, design changes, etc., based on the knowledge of a skilled person, and such modifications are also within the scope of the present invention.

What is claimed is:

1. An adsorption method for adsorbing a substance, comprising:
    adsorbing the substance on a tube-shaped apatite crystal;
    wherein the tube-shaped apatite crystal is a monocrystal given by general formula $M^2{}_5(PO_4)_3X$, whereby $M^2$ represents at least one element selected from the group consisting of divalent alkali earth metals and Eu, and whereby X represents at least one element selected from the group consisting of halogen elements,
    wherein an outer form of the apatite crystal is a hexagonal prism in which an aperture of a hole formed on a top surface or bottom surface of the hexagonal prism is hexagonal, and
    wherein at least one interior lateral surface of an interior wall of the hole is comprised of one monocrystal.

2. The adsorption method according to claim 1, wherein an inner diameter of the tube-shaped apatite crystal is 10 nm to 10 μm.

3. An adsorption separation method comprising:
    adsorbing protein or amino acid on a tube-shaped apatite crystal; and
    causing the apatite crystal on which the protein or amino acid is adsorbed to contact an aqueous chloride solution, and
    selectively isolating the adsorbed protein or amino acid;
    wherein the tube-shaped apatite crystal is a monocrystal given by a general formula $M^2{}_5(PO_4)_3X$, whereby $M^2$ represents at least one element selected from the group consisting of divalent alkali earth metals and Eu, and whereby X represents at least one element selected from the group consisting of halogen elements,
    wherein an outer form of the apatite crystal is a hexagonal prism in which an aperture of a hole formed on a top surface or bottom surface of the hexagonal prism is hexagonal, and
    wherein at least one interior lateral surface of an interior wall of the hole is comprised of one monocrystal.

4. A drug delivery carrier comprising a tube-shaped apatite crystal and a drug carried by the tube-shaped apatite crystal;
    wherein the tube-shaped apatite crystal is a monocrystal given by a general formula $M^2{}_5(PO_4)_3X$, whereby $M^2$ represents at least one element selected from the group consisting of divalent alkali earth metals and Eu, and whereby X represents at least one element selected from the group consisting of halogen elements,
    wherein an outer form of the apatite crystal is a hexagonal prism in which an aperture of a hole formed on a top surface or bottom surface of the hexagonal prism is hexagonal, and
    wherein at least one interior lateral surface of an interior wall of the hole is comprised of one monocrystal.

5. The drug delivery carrier according to claim 4, wherein a drug is carried inside the tube-shaped apatite crystal.

6. The drug delivery carrier according to claim 4, wherein an inner diameter of the tube-shaped apatite crystal is 10 nm to 50 μm.

7. An adsorption method according to claim 1, comprising:
    filing a column with the tube-shaped apatite crystal; and
    passing a fluid containing the substance through the column.

* * * * *